United States Patent
Dong et al.

(10) Patent No.: US 12,422,391 B2
(45) Date of Patent: Sep. 23, 2025

(54) RUGGEDIZED SENSOR FOR DETECTING ORGANIC LIQUIDS

(71) Applicant: nVENT Services GmbH, Schaffhausen (CH)

(72) Inventors: Wesley Dong, Belmont, CA (US);
Jennifer Robison, Kelowna (CA);
Emmi Ngo, Santa Rosa, CA (US);
Peter Wijeratne, San Carlos, CA (US);
Johnny Lam, San Mateo, CA (US)

(73) Assignee: Chemelex Europe GmbH, Schaffhausen (CH)

( * ) Notice: Subject to any disclaimer, the term of this patent is extended or adjusted under 35 U.S.C. 154(b) by 777 days.

(21) Appl. No.: 17/005,094

(22) Filed: Aug. 27, 2020

(65) Prior Publication Data

US 2021/0063337 A1 Mar. 4, 2021

Related U.S. Application Data

(60) Provisional application No. 62/895,790, filed on Sep. 4, 2019, provisional application No. 62/892,441, filed on Aug. 27, 2019.

(51) Int. Cl.
*G01N 27/07* (2006.01)
*G01N 27/04* (2006.01)
*G01N 33/28* (2006.01)

(52) U.S. Cl.
CPC ........... *G01N 27/07* (2013.01); *G01N 27/045* (2013.01); *G01N 33/28* (2013.01)

(58) Field of Classification Search
CPC .... G01N 27/07; G01N 27/045; G01N 27/122; G01N 33/28
See application file for complete search history.

(56) References Cited

U.S. PATENT DOCUMENTS

| 4,333,067 A | 6/1982 | Kugimiya et al. |
| 4,450,428 A | 5/1984 | Ohta et al. |
| 4,478,067 A | 10/1984 | Ohta et al. |
| 4,487,057 A | 12/1984 | Lutz |

(Continued)

FOREIGN PATENT DOCUMENTS

| CN | 200962099 Y | 10/2007 |
| CN | 103604839 A | 2/2014 |

(Continued)

OTHER PUBLICATIONS

Yagi et al., English translation of JPH06265519A, 1994 (Year: 1994).*

(Continued)

*Primary Examiner* — Luan V Van
*Assistant Examiner* — Shizhi Qian
(74) *Attorney, Agent, or Firm* — Quarles & Brady LLP (57) ABSTRACT

An organic liquid sensor configured to output a signal corresponding to the presence of one or more organic liquids is provided. The sensor includes a circuit board, a sensor film deposited on the circuit board, the sensor film including a first length, a second length, and a bridge portion, the first length and the second length being electrically separated by a gap and the bridge portion being electrically coupled to the first length and the second length. The circuit board is configured to detect a resistance of the sensor film.

16 Claims, 8 Drawing Sheets

(56) References Cited

U.S. PATENT DOCUMENTS

| | | | |
|---|---|---|---|
| 4,608,232 A | 8/1986 | Sunano et al. | |
| 4,631,952 A * | 12/1986 | Donaghey | G01N 27/12 338/34 |
| 4,693,953 A | 9/1987 | Torikai | |
| 4,713,646 A | 12/1987 | Sunano | |
| 4,816,800 A | 3/1989 | Onaga et al. | |
| 4,855,706 A | 8/1989 | Hauptly | |
| 4,909,066 A | 3/1990 | Matsuura et al. | |
| 4,942,764 A | 7/1990 | Dews et al. | |
| 5,006,828 A | 4/1991 | Yutaka et al. | |
| 5,482,678 A | 1/1996 | Sittler | |
| 5,578,997 A | 11/1996 | Lechevalier | |
| 5,670,115 A | 9/1997 | Chen et al. | |
| 5,743,136 A | 4/1998 | Gaston et al. | |
| 6,615,659 B2 | 9/2003 | Shibue et al. | |
| 6,705,152 B2 | 3/2004 | Routkevitch et al. | |
| 7,025,849 B2 | 4/2006 | Kim et al. | |
| 7,033,457 B2 | 4/2006 | Kim et al. | |
| 7,113,069 B1 | 9/2006 | Sunshine | |
| 7,827,852 B2 | 11/2010 | Cui et al. | |
| 7,829,185 B2 | 11/2010 | Cuppoletti | |
| 7,859,273 B2 | 12/2010 | McCoy et al. | |
| 8,419,961 B2 | 4/2013 | Qin | |
| 8,429,952 B1 | 4/2013 | Bringhurst et al. | |
| 8,586,394 B2 | 11/2013 | Fosaaen | |
| 8,614,118 B2 | 12/2013 | Haji et al. | |
| 8,640,526 B2 | 2/2014 | Di Miro et al. | |
| 8,673,213 B2 | 3/2014 | Augstein et al. | |
| 8,677,803 B2 | 3/2014 | Hocken et al. | |
| 8,739,604 B2 | 6/2014 | Krishna et al. | |
| 8,823,400 B2 | 9/2014 | Hocken et al. | |
| 9,042,075 B2 | 5/2015 | Borini et al. | |
| 9,523,651 B2 | 12/2016 | Humbert et al. | |
| 9,855,359 B2 | 1/2018 | Liu | |
| 10,018,581 B2 | 7/2018 | Wang et al. | |
| 10,175,221 B2 | 1/2019 | Ciampini | |
| 10,302,635 B2 | 5/2019 | Kobayashi | |
| 2009/0029403 A1 | 1/2009 | Fleischer et al. | |
| 2009/0090179 A1 | 4/2009 | Carmona et al. | |
| 2009/0130421 A1 | 5/2009 | Ramamurthy | |
| 2010/0025238 A1 | 2/2010 | Gottlieb et al. | |
| 2010/0219849 A1* | 9/2010 | McCoy | G01N 27/122 324/693 |
| 2011/0045601 A1* | 2/2011 | Gryska | G01N 27/221 422/82.01 |
| 2012/0156688 A1 | 6/2012 | McAlpine et al. | |
| 2012/0220041 A1* | 8/2012 | Colla | G01N 27/221 422/69 |
| 2012/0323098 A1* | 12/2012 | Moein | A61B 5/1486 29/832 |
| 2016/0238548 A1 | 8/2016 | Aguir et al. | |
| 2017/0010258 A1 | 1/2017 | Davis et al. | |
| 2018/0038815 A1 | 2/2018 | Gu et al. | |

FOREIGN PATENT DOCUMENTS

| | | | |
|---|---|---|---|
| CN | 106687811 A | 5/2017 | |
| CN | 107144370 A | 9/2017 | |
| EP | 1953539 B1 | 12/2017 | |
| JP | S57133345 A | 8/1982 | |
| JP | H06265519 A * | 9/1994 | |
| JP | 5936087 B2 | 5/2016 | |
| KR | 2006021822 A | 3/2006 | |
| WO | 9428372 A1 | 12/1994 | |
| WO | 0233732 A2 | 4/2002 | |
| WO | 03012390 A2 | 2/2003 | |
| WO | 2005073703 A1 | 8/2005 | |
| WO | 2007065163 A2 | 6/2007 | |
| WO | 2018126326 A1 | 7/2018 | |
| WO | 2019053460 A1 | 3/2019 | |
| WO | WO-2019046961 A1 * | 3/2019 | G01M 3/18 |

OTHER PUBLICATIONS

NVent|Raychem, Fast Fuel Sensor Probe with Leader Cable, No Connector, specifications, Copyright 2020 nVent, 2 pages.

* cited by examiner

RUGGEDIZED SENSOR FOR DETECTING ORGANIC LIQUIDS

CROSS-REFERENCES TO RELATED APPLICATIONS

This application is based on, claims the benefit of, and claims priority to, U.S. Provisional Patent Application No. 62/895,790, filed Sep. 4, 2019, and U.S. Provisional Patent Application No. 62/892,441, filed Aug. 27, 2019, which are hereby incorporated herein by reference in their entirety for all purposes.

BACKGROUND

Certain sensors can be used to detect organic liquids in the presence of other substances. For example, certain sensors can be used to detect hydrocarbons and/or oils in the presence of water, such as hydrocarbon fuel floating on water, spreading on a flat surface, or collecting in a sump. Such sensors can also be used to improve the safety of diesel generators used for back-up electrical power by detecting potential leaks. The sensors may be used for the same purpose of detecting leaks near oil storage tanks used to fuel boilers or other heating related equipment in commercial buildings. The sensors can also be used to detect hydrocarbons and/or oils at a range of temperatures as well as in dry conditions without water.

It is important that the sensors do not respond to water because the sensors may be placed in contact with water in a sump or placed outdoors (e.g., and be subjected to rain). The sensors can be configured to detect potential hydrocarbons and/or oils by changing a value of an electrical property, such as a resistance of the sensor, in the presence of the hydrocarbons and/or oil. Water, whether alone or in addition to the hydrocarbons and/or oil, should not have a significant effect on the electrical property being detected.

Additionally, the sensors may be corroded or otherwise damaged by extensive contact with water. Once corroded, the sensors may not function properly at the originally specified range of temperatures and/or wet and dry conditions.

SUMMARY

The invention addresses the need for a sensor configured to detect hydrocarbons and/or oils in wet and dry conditions at a range of temperatures while providing greater protection against corrosion and/or abrasion than previous sensors.

In some embodiments, an organic liquid sensor configured to output a signal corresponding to the presence of one or more organic liquids is provided. The sensor includes a circuit board and a sensor film deposited on the circuit board. The sensor film comprises a first length, a second length, and a bridge portion. The first length and the second length are electrically separated by a gap and the bridge portion is electrically coupled to the first length and the second length. Furthermore, the circuit board is configured to detect a resistance of the sensor film.

In some embodiments, an organic liquid monitoring system is provided. The system includes a controller and an organic liquid sensor. The controller comprises a memory and a processor. The organic liquid sensor is configured to output a signal corresponding to the presence of one or more organic liquids and includes a circuit board. The circuit board is configured to detect a resistance of a sensor film deposited on the circuit board. The sensor film comprises a first length, a second length, and a bridge portion, where the first length and the second length are electrically separated by a gap and the bridge portion is electrically coupled to the first length and the second length. Furthermore, the controller is coupled to the organic liquid sensor and configured to receive the signal corresponding to the presence of one or more organic liquids.

In some embodiments, an organic liquid sensor configured to output a signal corresponding to the presence of one or more organic liquids is provided. The organic liquid sensor includes a circuit board, an electronic monitoring circuit comprising a first terminal and a second terminal, and a sensor film. The sensor film is deposited on the circuit board and includes a first length, a second length, and a bridge portion. The first terminal is electrically coupled to the first length, and the second terminal is electrically coupled to the second length, where the first terminal, the first length, the bridge portion, the second length, and the second terminal are electrically coupled in series without exposed conductive metals.

DETAILED DESCRIPTION

Figure 1:
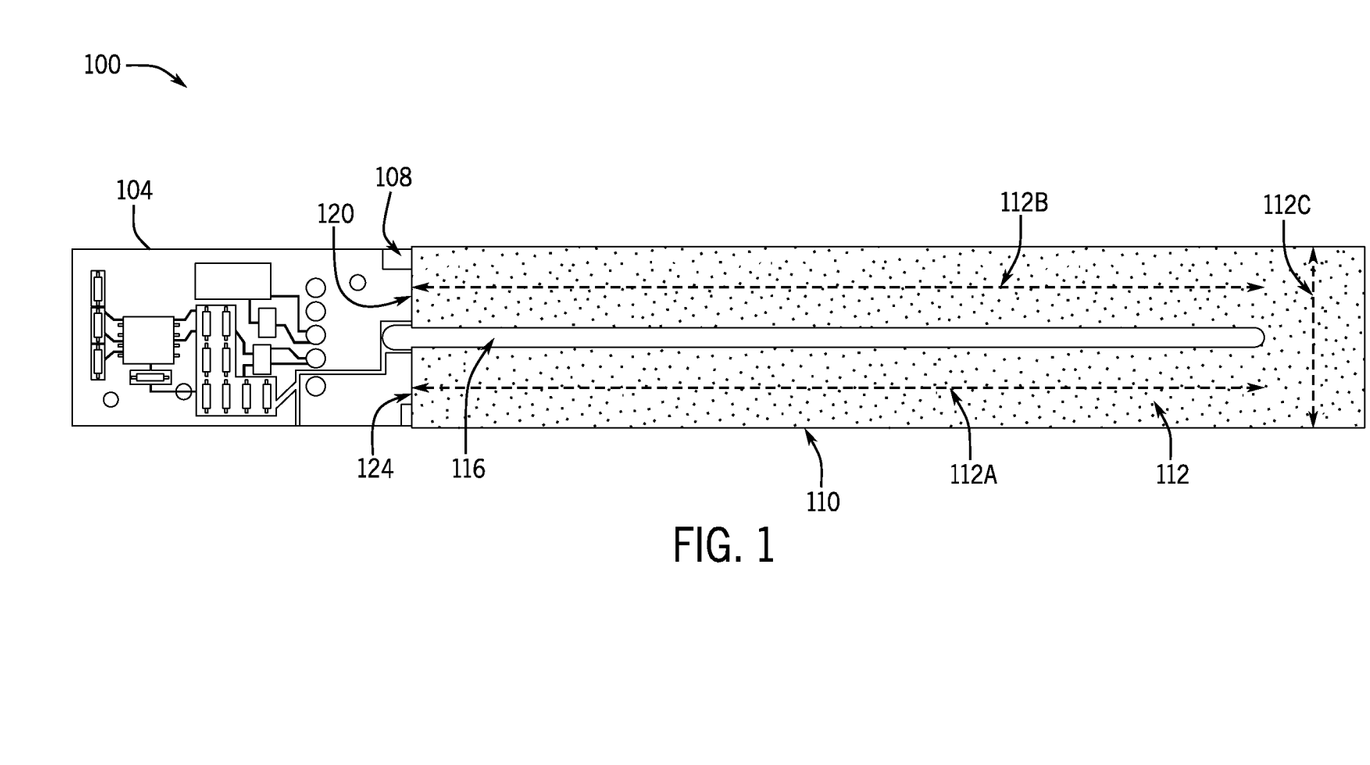
FIG. 1 shows a view of a sensor according to some embodiments of the invention.

FIG. 1 illustrates a sensor 100 according to some embodiments of the invention. As will be described in detail below, the sensor 100 can include various electrical components configured to sense organic liquids including, but not limited to, diesel fuel, gasoline, and/or jet fuel, and output a signal indicative of a presence of such organic fluids and/or a relative concentration of the organic liquids. As shown in FIG. 1, the sensor 100 can include a circuit board 104, such as a printed circuit board, an electronic monitoring circuit 108, and a sensing component 110 including a sensor film 112.

In some embodiments, the electronic monitoring circuit 108 can include one or more resistors, capacitors, operational amplifiers, diodes, connectors such as jumpers, and/or other electrical components mounted to the circuit board 104, for example, via throughhole and/or surface mounting methods, as are known in the art. The electronic monitoring circuit 108 can be configured to receive power from an external source and/or output a signal indicative of whether or not organic fluids are present on the sensor 100 and/or a relative concentration of the sensed organic liquids via one or more connectors. In some embodiments, the electronic monitoring circuit 108 can be encapsulated by a non-conductive material such as an epoxy in order to protect the electronic monitoring circuit 108 from electrical shorts due to water or other environmental factors.

The sensor 100 can further include the sensing component 110 with the sensor film 112 deposited on and coupled to a substrate. In some embodiments, the substrate can be the circuit board 104, or a layer such as a primer layer (not shown) deposited on and coupled to the circuit board 104. As shown in FIG. 1, the electronic monitoring circuit 108 can be coupled to the sensor film 112 at a first terminal 120 and a second terminal 124. The sensor film 112 can be formed from one or more materials, such as from an elastomer that is filled with conductive particles. Additionally, in some embodiments, the sensor film 112 can be formed from a fungicide or mildewcide mixed in with the elastomer that is filled with conductive particles in order to increase the anti-fungal properties of the sensor 100, as further described below.

Functionally, the sensor film 112 may swell in the presence of the organic hydrocarbons or oils to be detected, and the subsequent increase in resistance of the sensor film 112 caused by such swelling is detected and processed by the associated electronic monitoring circuit 108. More specifically, the electronic monitoring circuit 108 can be configured to sense the resistance between the first terminal 120 and the second terminal 124. Furthermore, the electronic monitoring circuit 108 can be configured to output a signal corresponding to the resistance between the first terminal 120 and the second terminal 124. This resistance can change based on the presence of the organic hydrocarbons or oils to be detected as a result of such substances causing the sensor film 112 to swell, which affects connections between the conductive particles. As a result, for example, a sensed resistance above a threshold resistance value may indicate a presence of organic hydrocarbons or oils. In a further example, a magnitude of the sensed resistance can be correlated to a relative concentration of such organic hydrocarbons or oils.

In order to provide a fast detection signal (i.e., to respond quickly to the presence of organic fluids), the sensor film 112 can be thinly deposited on the circuit board 104. Furthermore, in some embodiments, the sensor film 112 can be deposited on a single side of the circuit board 104, which may increase the corrosion resistance of the sensor 100, as will be explained below. In some embodiments, the sensor film 112 can be deposited on top of the primer layer deposited on top of the circuit board 104. The sensor film 112 and/or the primer layer may only be deposited on a nonconductive portion of the surface of the circuit board 104. For example, the nonconductive portion can include surfaces where a resin covers copper layers of the circuit board 104.

The present disclosure provides for organic liquid sensors, such as the sensor 100, that may provide more corrosion resistance than previous sensors. As will be explained below, the corrosion resistance of the sensor 100 can be increased by depositing the sensor film 112 in a "horseshoe" pattern or "U-shape" pattern on a single side of the circuit board 104. Additionally or alternatively, the corrosion resistance of the sensor 100 can be increased by surface etching or otherwise treating the surface of the circuit board 104 before a primer layer and/or the sensor film 112 are deposited.

For example, the sensor film 112 can be deposited on and coupled to the circuit board 104 and/or primer layer in a general horseshoe pattern or U-shape pattern, which can increase the corrosion resistance of the sensor 100 by eliminating exposed materials that may be prone to corrosion. As shown in FIG. 1, the sensor film 112 can include a first length 112A, a second length 112B, and a bridge portion 112C forming the U-shape. The first length 112A and the second length 112B can be physically and electrically separated by a gap 116. In particular, the first length 112A and the second length 112B can be physically and electrically separated at least near the first terminal 120 and the second terminal 124. In some embodiments, the gap 116 can extend through the circuit board 104 and/or the primer. In some embodiments, the gap 116 can be created by depositing a mask on a portion of the circuit board 104 or the primer, depositing the sensor film 112 on the circuit board 104, the primer, and/or the mask, and removing the mask. The bridge portion 112C physically and electrically connects the first length 112A and the second length 112B. In other words, the bridge portion 112C is electrically coupled to the first length 112A and the second length 112B. The separation caused by the gap 116 allows current to travel through the sensor film 112 from the first terminal 120 to the second terminal 124 (or alternatively from second terminal 124 to the first terminal 120), allowing the resistance of the sensor film 112 to be determined.

Furthermore, the sensor film 112 can be coupled to the first terminal 120 and the second terminal 124 without the use of a conductive bridge made from a material prone to potential corrosion. In some embodiments, the sensor film 112 can be deposited immediately on top of the first terminal 120 and the second terminal 124, each of which can include a pad made from a conductive material such as copper. In embodiments that include a primer layer, the primer layer may only be deposited on the nonconductive portion of the surface of the circuit board 104, allowing the sensor film to be directly coupled to the first terminal 120 and the second terminal 124. Furthermore, the design of the sensor film 112 may significantly reduce or eliminate entirely any exposed conductive materials (e.g., conductive metals such as copper, silver, etc.) from the surface of the sensor 100, leaving only non-conductive portions of the circuit board 104 (which can include resin) and the sensor film 112 exposed to the outside environment. The reduction or elimination of exposed conductive materials can improve the corrosion resistance of the sensor 100 in certain conditions, such as when the sensor 100 is exposed to and/or submerged in saltwater. Thus, in some embodiments, the first terminal 120, the first length 112A, the bridge portion 112C, the second length 112B, and the second terminal 124 are electrically coupled in series without any exposed conductive metals.

Additionally, in some embodiments, the circuit board 104 in order to increase the corrosion resistance and ruggedness of the sensor 100. In one example, the circuit board 104 can be treated using a technique such as plasma treatment before a primer layer is deposited. The treatment can activate the surface of the circuit board 104, which can improve the adhesion of the primer layer. Furthermore, the treatment can potentially physically roughen the surface of the circuit board 104, but may not be required for improved adhesion. Furthermore, in addition or alternatively to the above, other physical roughening treatments (e.g., mechanical abrasion) or chemical roughening treatments (e.g., other primers or coupling agents) can be applied to the surface of the circuit board 104. Once treated via one or more of the above treatments, the surface of the circuit board 104 can be referred to as a treated surface.

After the primer layer has been deposited onto the treated surface, the sensor film 112 can then be deposited on top of the primer layer and/or the circuit board 104. Treating the circuit board 104 can improve adhesion of the sensor film 112 to the primer layer and/or circuit board 104. The improved adhesion has also been shown to increase the overall corrosion resistance of the sensor 100. Additionally, the adhesion improvement treatment of the circuit board 104 may also increase the durability of the sensor in freeze/thaw conditions, which can be common in certain locations where organic liquid sensors are used. Lastly, treating the circuit board 104, as well as reducing and/or eliminating exposed conductive materials, as described above, may allow the sensor 100 to function for extended periods of time in saltwater, which is generally more corrosive than freshwater. It is contemplated that a top layer (such as a protective coating or film) could be applied on top of the sensor film 112 in order to further protect the sensor film 112 without interfering with the organic liquid sensing capabilities of the sensor 100.

Treating the circuit board 104 to improve adhesion and/or depositing a primer layer can still allow the sensor film 112 to be deposited as a thin layer, as with previous sensors, and therefore does not significantly affect the organic liquid sensing performance of the sensor 100. In some embodiments, the sensor 100 can detect as little as 2 mm of a fuel floating on top of water. Additionally, the sensor 100 can detect certain light or middleweight fuels such as diesel fuel, jet fuel, or gasoline in as little as two seconds, and can be approved under the FM 7745 approval standard for diesel fuel detection in less than thirty seconds. The sensor 100 can accurately detect the presence of organic liquids in the presence of water. In some embodiments, the sensor film 112 can include one or more materials (e.g., an elastomer that is filled with conductive particles, as noted above) configured to absorb the organic liquid(s) while repelling the water. Thus, in some embodiments, the sensor film 112 can be generally hydrophobic.

In some embodiments, in order to provide protection against mildew and/or fungus, the sensor film 112 can be formed from a fungicide or mildewcide mixed in with the elastomer that is filled with conductive particles. For example, in some embodiments, a mildewcide such as MX-3 distributed by CFI Products can be mixed in with the elastomer filled with conductive particles to form a preliminary mixture that can be deposited to form the sensor film 112. MX-3 contains an active ingredient 3-Iodo-2-Propynyl Butylcarbamate, shown in equation (1) below:

If the mildewcide is mixed in to the elastomer at an approximate percentage, such as 1.3% to 2.5% weight of the preliminary mixture if the mildewcide is MX-3, the organic liquid sensing performance of the sensor 100 can be minimally affected, while the fungus and/or mildew growth resistance of the sensor 100 can be significantly improved. Once the preliminary mixture has dried and formed the sensor film 112, the final concentration of the mildewcide in the sensor film 112 may differ from the concentration in the preliminary mixture. In the case that MX-3 is used as the mildewcide, the final concentration by weight in the sensor film 112 may include 3.4% to 6.6% mildewcide by weight.

An advantage of using MX-3 as the mildewcide is that MX-3 is easily mixed in with other components of the preliminary mixture of the sensor film 112. For example, in preliminary mixtures including Xylene, silicone, and graphite materials, MX-3 is easily dispersed in the Xylene at a temperature of 70° F. (i.e., room temperature). It is contemplated that fungicides and/or mildewcides other than MX-3 could be used as long as the chosen fungicide and/or mildewcide is easily dispersed in one or more liquid ingredients (such as Xylene) for relatively uniform dispersion throughout the sensor film 112.

Figure 2A:
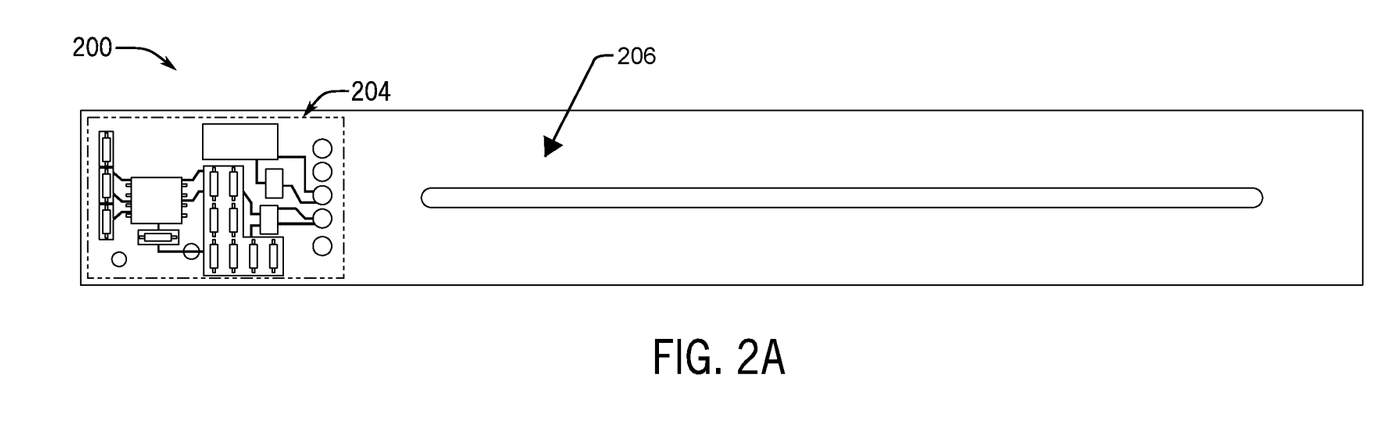
FIG. 2A shows a top view of a circuit board schematic according to some embodiments of the invention.
Figure 2B:
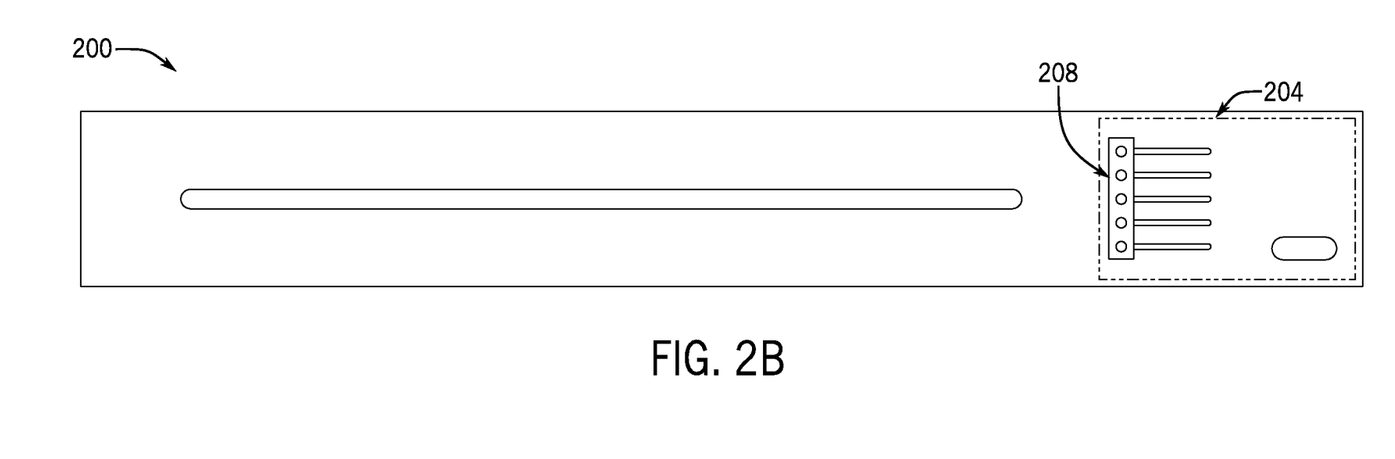
FIG. 2B shows a bottom view of the circuit board schematic of FIG. 2A according to some embodiments of the invention.

Referring to FIG. 2A and FIG. 2B, a top view and a bottom view, respectively, of a circuit board schematic are shown. In some embodiments, the circuit board 200 of FIGS. 2A and 2B can be the same as the circuit board 104 described above with respect to FIG. 1. For example, an electronic monitoring circuit 204 including one or more resistors, capacitors, operational amplifiers, diodes, connectors such as jumpers, and/or other electrical components can be mounted to the circuit board 200 via throughhole and/or surface mounting methods, as are known in the art. In particular, the electronic monitoring circuit 204 can include a connector 208 mounted to the bottom of the circuit board 200, as shown in FIG. 2B, while other components included in the electronic monitoring circuit 204 can be mounted to the top of the circuit board 200, as shown in FIG. 2A.

The circuit board 200 can include a flat surface 206 that a portion of a sensor film (e.g., the sensor film 112 in FIG. 1) can be arranged on. In some embodiments, at least some of the first length 112A, the second length 112B, and the bridge portion 112C can be arranged on the flat surface 206. In some embodiments, the entire sensor film 112 including the entire first length 112A, the entire second length 112B, and the entire bridge portion 112C can be arranged on the flat surface 206.

Figure 3:
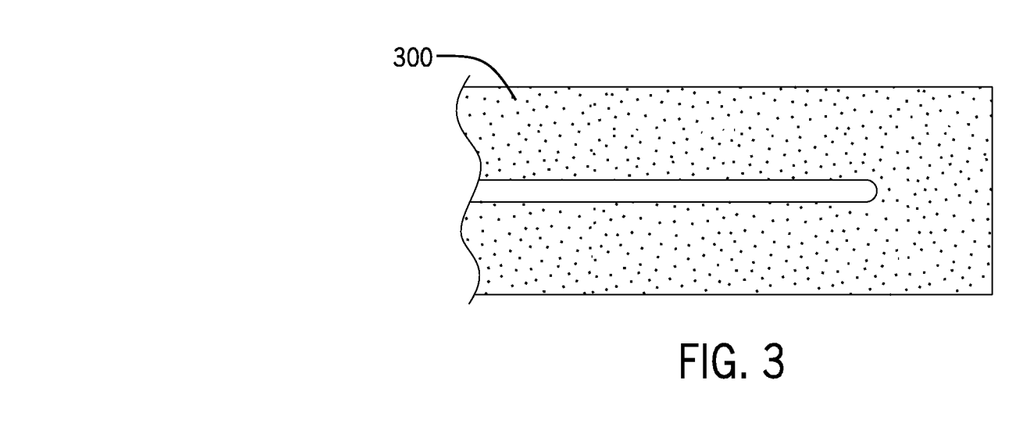
FIG. 3 shows a partial top view of an organic liquid sensor according to some embodiments of the invention after a corrosion test.

Referring to FIG. 3, a portion of an organic liquid sensor 300 after a corrosion test is shown. The organic liquid sensor 300 includes a sensor film disposed on a single surface, formed as a U-shape, and manufactured by roughening a circuit board before a primer layer is deposited, followed by the sensor film being deposited on top of the primer layer (as described above). The organic liquid sensor 300 did not exhibit significant corrosion as a result of the corrosion test, likely due to the features described above.

Figure 4:
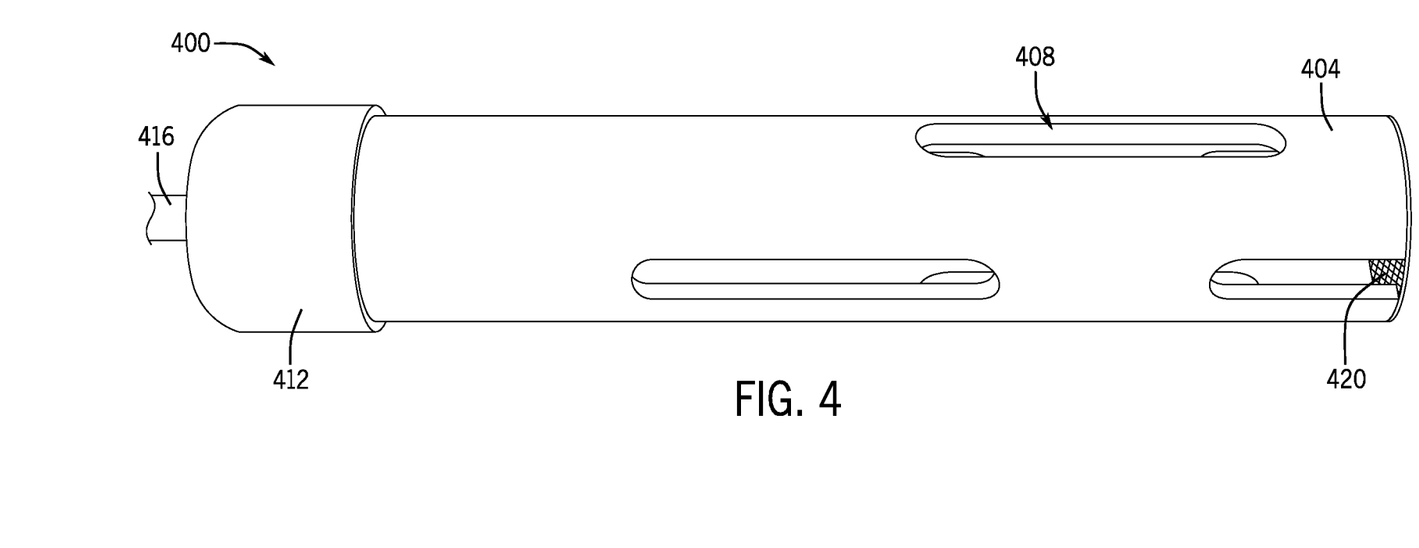
FIG. 4 shows a side view of a sensor assembly according to some embodiments of the invention.

Referring to FIG. 4, a sensor assembly 400, according to some embodiments, is shown. The sensor assembly 400 can be used to detect organic liquids containing hydrocarbons such as, but not limited to, gasoline, jet fuel, diesel fuel and/or oils at a range of temperatures (e.g., −40° C. to 85° C.) in wet conditions and dry conditions without water. The sensor assembly 400 can include a sensor (not shown) such as the sensor 100 described above with respect to FIG. 1. The sensor assembly 400 can include a housing including a housing tube 404, an end cap 412, and a mesh 420. The sensor can be positioned inside the housing. The housing can then provide mechanical protection such as abrasion protection to the sensor assembly 400. In some embodiments, the housing tube 404 can be made from a rigid plastic or other rigid material resistant to water and that does not interfere with the ability of the sensor to detect of organic liquids.

The housing tube 404 can include one or more openings 408. The openings 408 can be sized large enough to allow a fluid such as water and/or an organic liquid to reach the sensor while being sized small enough to allow the housing tube 404 to protect the sensor from other physical damage (e.g., from elements such as rocks). The mesh 420 can be coupled to a distal end of the housing tube 404 opposite the end cap 412. The mesh 420 can be sized in order to protect the sensor from rocks and other debris while allowing the sensor access to fluids such as water and/or organic liquids.

The housing tube 404 can be coupled to the end cap 412. The end cap 412 can be further coupled to, or provide a passageway for, a jumper cable 416 in electrical communication with the sensor. More specifically, the jumper cable 416 can be coupled to a connector of a circuit, such as the electronic monitoring circuit 108 described above. The jumper cable 416 can be coupled to and in communication with a controller (not shown) in order to provide power to the sensor and/or provide a signal from the sensor to the controller.

Figure 5A:
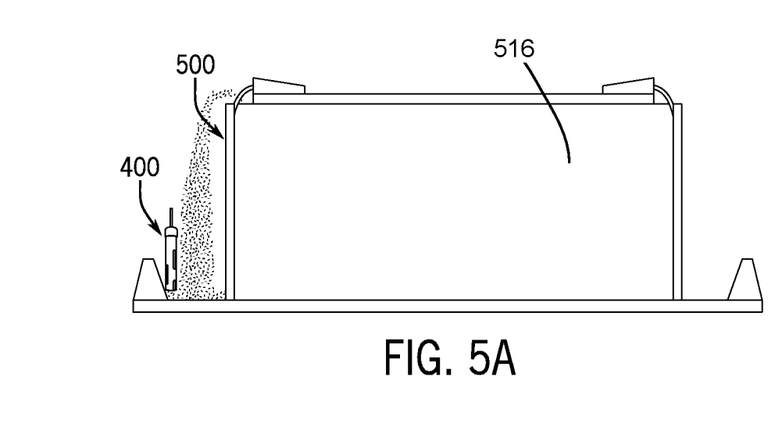
FIG. 5A shows the sensor assembly of FIG. 4 positioned outside of a tank that has overflown.

The sensor assembly 400 can be used in a variety of different environments. For example, referring FIGS. 5A, 5B, 5C, and 5D, various environments in which the sensor assembly 400 can be used are shown. FIG. 5A shows the sensor assembly 400 positioned outside of a tank 500 that has overflown. When the tank 500 overflows, the sensor assembly 400 can detect if a liquid 516 overflowing the tank 500 contains certain organic liquids.

Figure 5B:
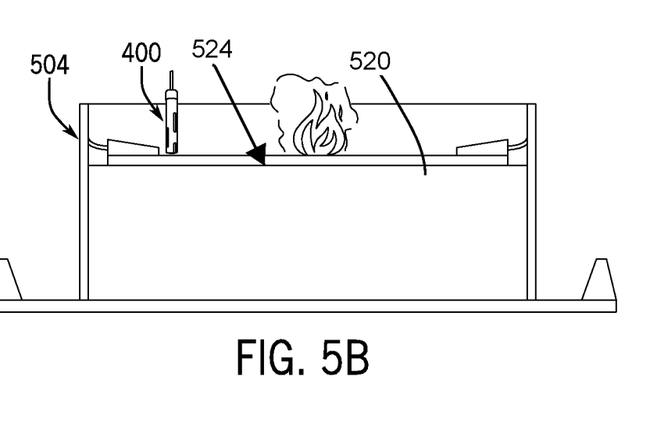
FIG. 5B shows the sensor assembly of FIG. 4 positioned near the crest of a liquid being held in a tank.

FIG. 5B shows the sensor assembly 400 positioned near a crest 524 of a liquid 520 being held in a tank 504. If certain organic liquids are present in the tank, the organic liquids may float to the top of the tank. The sensor assembly 400 can then detect if the tank 504 has been contaminated with certain organic liquids.

Figure 5C:
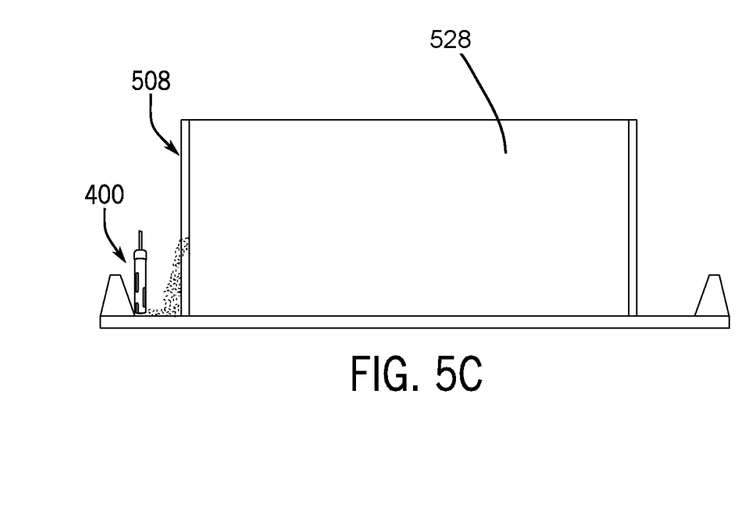
FIG. 5C shows the sensor assembly of FIG. 4 positioned outside of a tank that has a leak.

FIG. 5C shows the sensor assembly 400 positioned outside of a tank 508 that has a leak. When the tank 504 leaks, the sensor assembly 400 can detect if a liquid 528 leaking from the tank 504 contains certain organic liquids.

Figure 5D:
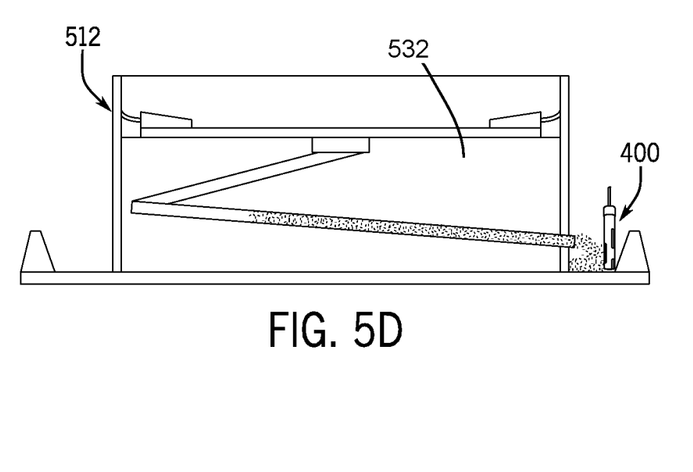
FIG. 5D shows the sensor assembly of FIG. 4 positioned outside of a tank that purposefully discharges a liquid being held in the tank.

FIG. 5D shows the sensor assembly 400 positioned outside of a tank 512 that purposefully discharges a liquid 532 being held in the tank 512. When the tank 512 is discharging the liquid 532, the sensor assembly 400 can detect if the liquid 532 contains certain organic liquids.

Figure 6:
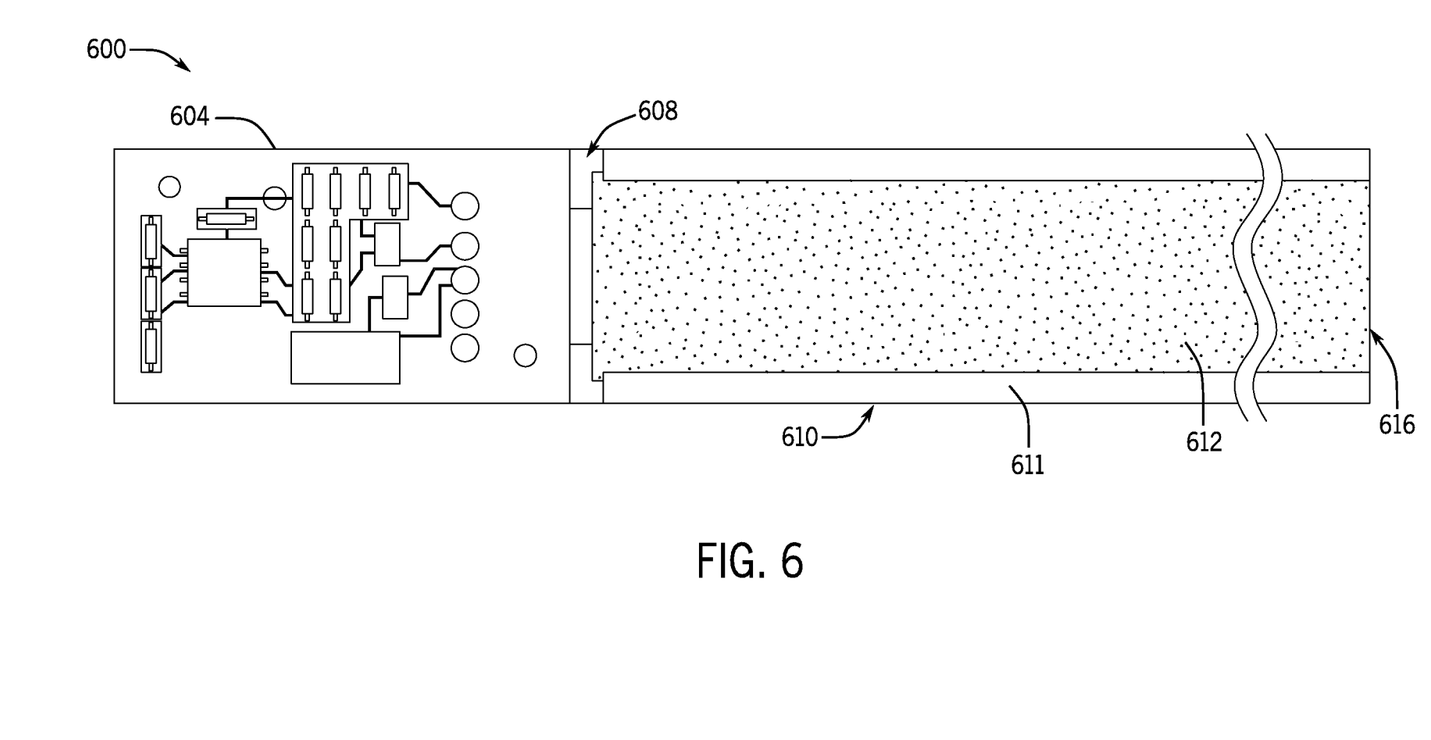
FIG. 6 shows a view of another sensor according to some embodiments of the invention.

Referring to FIG. 6, another sensor 600, according to some embodiments, is shown. As will be described in detail below, the sensor 600 can include various electrical components configured to sense organic liquids including diesel fuel, gasoline, and/or jet fuel, and output a signal indicative of whether or not organic fluids are present and/or a relative concentration of the organic liquids. As shown in FIG. 6, the sensor 600 can include a circuit board 604 such as a printed circuit board, an electronic monitoring circuit 608, and a sensing component 610.

The electronic monitoring circuit 608 can include one or more resistors, capacitors, operational amplifiers, diodes, connectors such as jumpers, and/or other electrical components mounted to the circuit board 604, for example, via throughhole and/or surface mounting methods as are known in the art. The electronic monitoring circuit 608 can be configured to receive power from an external source and/or output a signal indicative of whether or not organic fluids are present and/or a relative concentration of the organic liquids via one or more connectors. In some embodiments, the electronic monitoring circuit 608 can encapsulated by a non-conductive material such as an epoxy in order to protect from electrical shorts due to water or other environmental factors.

As shown in FIG. 6, the sensing component 610 can include a first sensor film layer 612 deposited on and coupled to a substrate 611. The substrate 611 can be a first surface of the circuit board 604. The electronic monitoring circuit 608 can be coupled to the first sensor film layer 612. Furthermore, the electronic monitoring circuit 608 can be coupled to a second sensor film layer (not shown) deposited on a second surface of the circuit board 604 opposite the first surface.

The first sensor film layer 612 and the second film layer can be coupled to each other by a bridging electrode (not shown) constructed of a conductive material such as copper, silver, gold, platinum, etc. The bridging electrode may be formed by leaving a conductive trace on each side of the circuit board 604 adjacent to a second end 616 of the circuit board 604. The conductive traces adjacent to the second end 616 of the circuit board may be electrically coupled, e.g., via plated through holes, jumpers, etc. The first sensor film layer 612, the bridging electrode and the second film sensor layer then form an electrical path from a first terminal or node of the electronic monitoring circuit 608 to a second terminal or node of the electronic monitoring circuit 608, and the electronic monitoring circuit 608 can be configured to sense the resistance of the electrical path.

The first sensor film layer 612 and the second film layer can be formed from the same materials as the sensor film 112 described above. In particular, the first sensor film layer 612 and the second film layer can be formed from materials including a mildewcide such as MX-3. In order to provide a fast detection signal (i.e., respond quickly to the presence of organic fluids), the first sensor film layer 612 and the second film layer can each be thinly deposited on the circuit board 604.

Figure 7A:
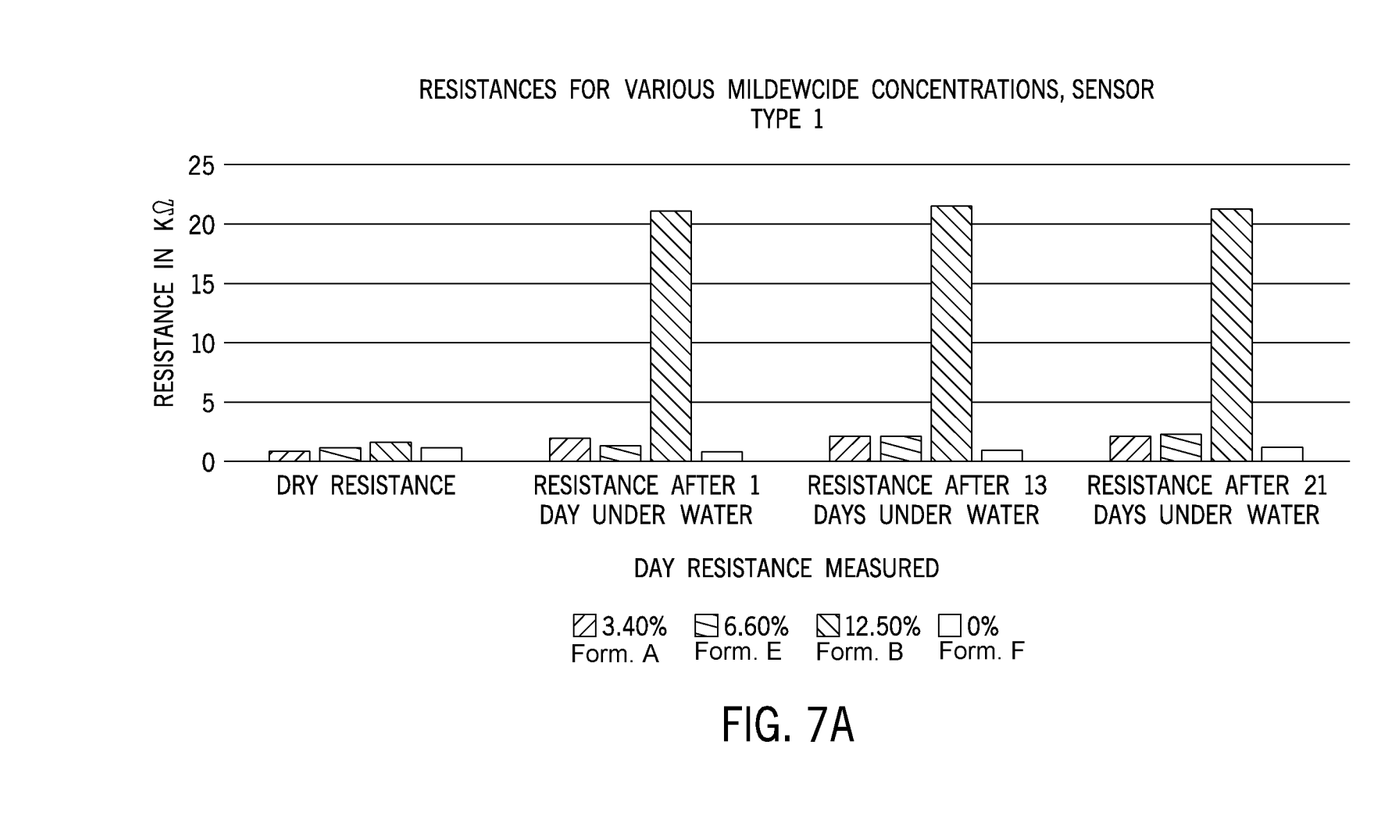
FIG. 7A shows a graph of resistances for sensors with various mildewcide concentrations for a first sensor type according to some embodiments of the invention.
Figure 7B:
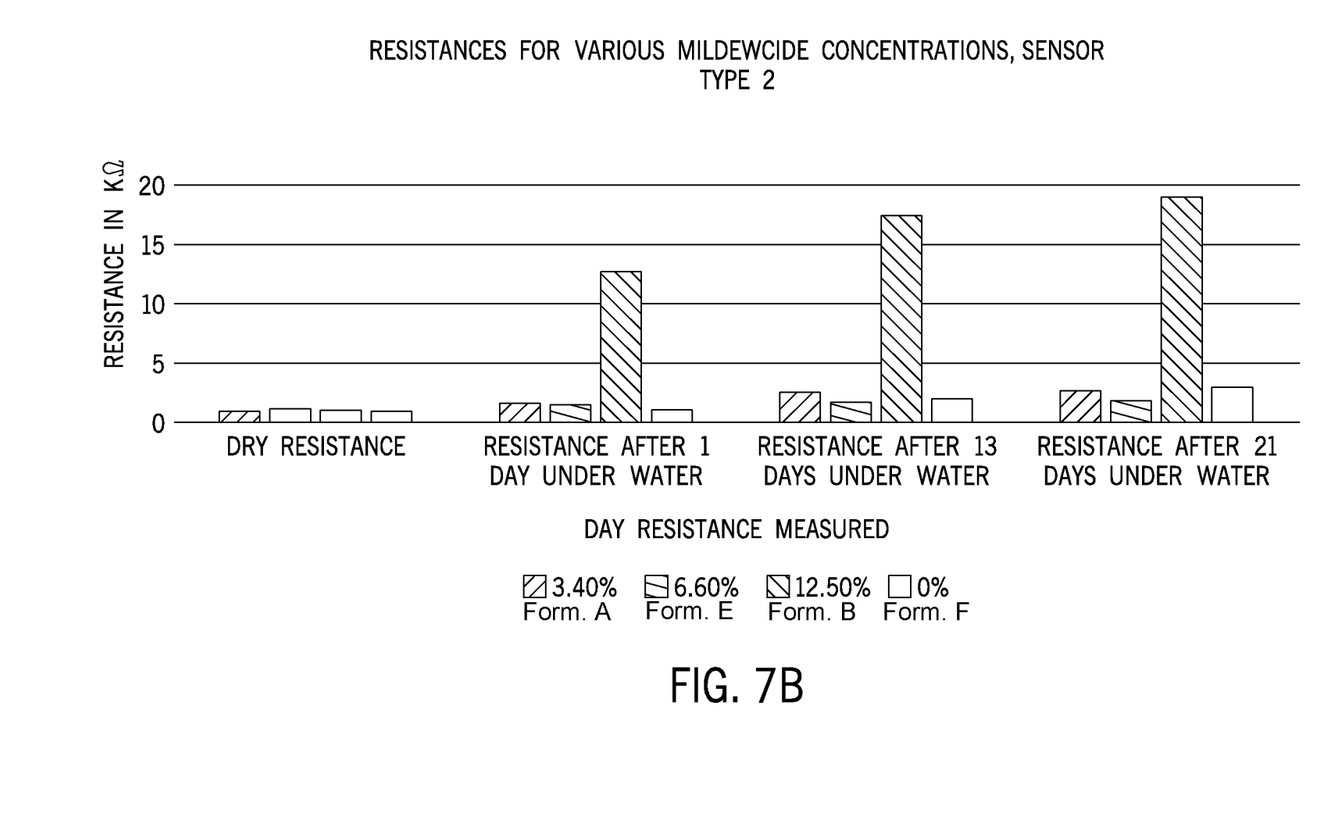
FIG. 7B shows a graph of resistances for sensors with various mildewcide concentrations for a second sensor type according to some embodiments of the invention.

Referring now to FIG. 7A and FIG. 7B, resistance values of various sensors during a testing period are shown. More specifically, various sensor film formulations were tested with varying concentrations of mildewcide, specifically MX-3. Sensors with formulation "A" had sensor films containing Xylene, Dow 1-2620, graphite, and MX-3, the concentration of the MX-3 in the sensor film being 3.4% by weight when dried (i.e., a final concentration). Sensors with formulation "E" had sensor films containing Xylene, Dow 1-2620, graphite, and MX-3, the concentration of the MX-3 in the sensor film being 6.6% by weight when dried (i.e., a final concentration). Sensors with formulation "B" had sensor films containing Xylene, Dow 1-2620, graphite, and MX-3, the concentration of the MX-3 in the sensor film being 12.5% by weight when dried (i.e., a final concentration). Sensors with formulation "F" had sensor films containing Xylene, Dow 1-2620, graphite, and no amount of MX-3 (i.e., a concentration of 0%).

Each sensor formulation was used in sensors using two different construction types: Type 1 (results shown in FIG. 7A) and Type 2 (results shown in FIG. 7B). The "Type 1" construction type is a sensor including multiple sensor film layers, such as the sensor 600 described above with respect to FIG. 6. The "Type 2" construction type is a sensor including a sensor film deposited on a single surface of the sensor, such as the sensor 100 described above with respect to FIG. 1.

As mentioned above, a sensor can sense the resistance of the sensor film in order to determine if organic liquids are present. More specifically, a threshold resistance value corresponding to organic liquids being present can be determined for each sensor film. In the cases of both Type 1 and Type 2 sensors without mildewcide, the threshold resistance value is 20 Kiloohms (KΩ). As will be explained below, adding mildewcide to the preliminary mixture of the sensor film at appropriate concentrations can minimally affect the resistance characteristics of the sensor film as compared to the sensor film without the mildewcide, allowing the mildewcide-enhanced sensors to be used with the same threshold resistance value.

As shown in FIGS. 7A and 7B, for each film formulation and sensor type, the "dry resistance" of the sensor film was measured. The dry resistance is the resistance of the dried sensor film before submersion in water. Every sensor was then submerged underwater for 21 days, with sensor film resistance measurements taken after 1 day underwater, 13 days underwater, and 21 days underwater. The resistance of the sensor film is important because if the resistance of a sensor film is too close the threshold resistance value without contact with organic fluids, the sensing performance of the sensor is diminished. As shown in FIGS. 7A and 7B, as well as Table 1 below (which shows the resistance values of the various formulations and sensor types), the resistance of the sensors with formulations A and E (with 3.4% and 6.6% mildewcide, respectively) did not differ significantly from the formulation F sensors (0% mildewcide) for both sensor types 1 and 2. Sensors with formulation B (12.5% mildewcide) showed significantly increased resistance compared to the other formulations, indicating the 12.5% concentration of mildewcide may be too high for applications to certain sensors.

| Film Formulation | Concentration of MX-3 (wt %) | Dry Type | Day Resistance (KΩ) | Resistance After 1 Day Under Water (KΩ) | Resistance After 13 Days Under Water (KΩ) | Resistance After 21 Days Under Water (KΩ) |
|---|---|---|---|---|---|---|
| A | 3.4 | Type 1 | 0.866 | 1.897 | 2.075 | 2.201 |
|   |     | Type 2 | 0.889 | 1.649 | 2.525 | 2.708 |
| E | 6.6 | Type 1 | 1.113 | 1.329 | 2.161 | 2.286 |
|   |     | Type 2 | 1.215 | 1.534 | 1.797 | 1.83 |
| B | 12.5 | Type 1 | 1.561 | 21.143 | 21.469 | 21.248 |
|   |     | Type 2 | 1.066 | 12.672 | 17.448 | 18.969 |
| F | 0 | Type 1 | 1.119 | 0.822 | 0.981 | 1.213 |
|   |   | Type 2 | 0.991 | 1.001 | 2.01 | 2.854 |

The sensors with formulations A, E, and F were then tested to determine how well the sensors could detect organic liquids after the 21-day submersion period. The response time of each sensor was measured by placing each sensor in contact with a fuel and timing how long the resistance of each sensor took to reach the threshold resistance value. The sensors with formulation F had an average response time of 35 seconds, the sensors with formulation A had an average response time of 21 seconds, and the sensors with formulation E had an average response time of 34 seconds. As such, all average response times were within a normal range of typical response times.

Based on the resistance test results, three samples of dried conductive film with formulation A (mildewcide concentration 3.4%), three samples of dried conductive film with formulation E (mildewcide concentration 6.6%), and three samples of dried conductive film with formulation F (0% mildewcide) were submitted for a resistance of synthetic polymeric materials to fungi test under ASTM G21-15. After 28 days of incubation, only the three samples with formulation F had any fungi growth, indicating that sensor films with a mildewcide concentration of 3.4% or 6.6% may prevent fungi growth better than sensor films without mildewcide.

In light of the above, sensors (such as sensor 100 or sensor 600 described above) including sensor films having a mildewcide concentration of 3.4-6.6% by dry weight may sense organic liquids with sufficient response time, as well as prevent fungi growth. It is contemplated that sensor films with a mildewcide concentration higher than 6.6% by dry weight and lower than 12.5% by dry weight may have acceptable resistance levels in water and sufficient response times to be used in an organic liquid sensor. It is further contemplated that sensor films with a mildewcide concentration lower than 3.4% by dry weight may have acceptable resistance levels in water and sufficient response times to be used in an organic liquid sensor.

Figure 8:
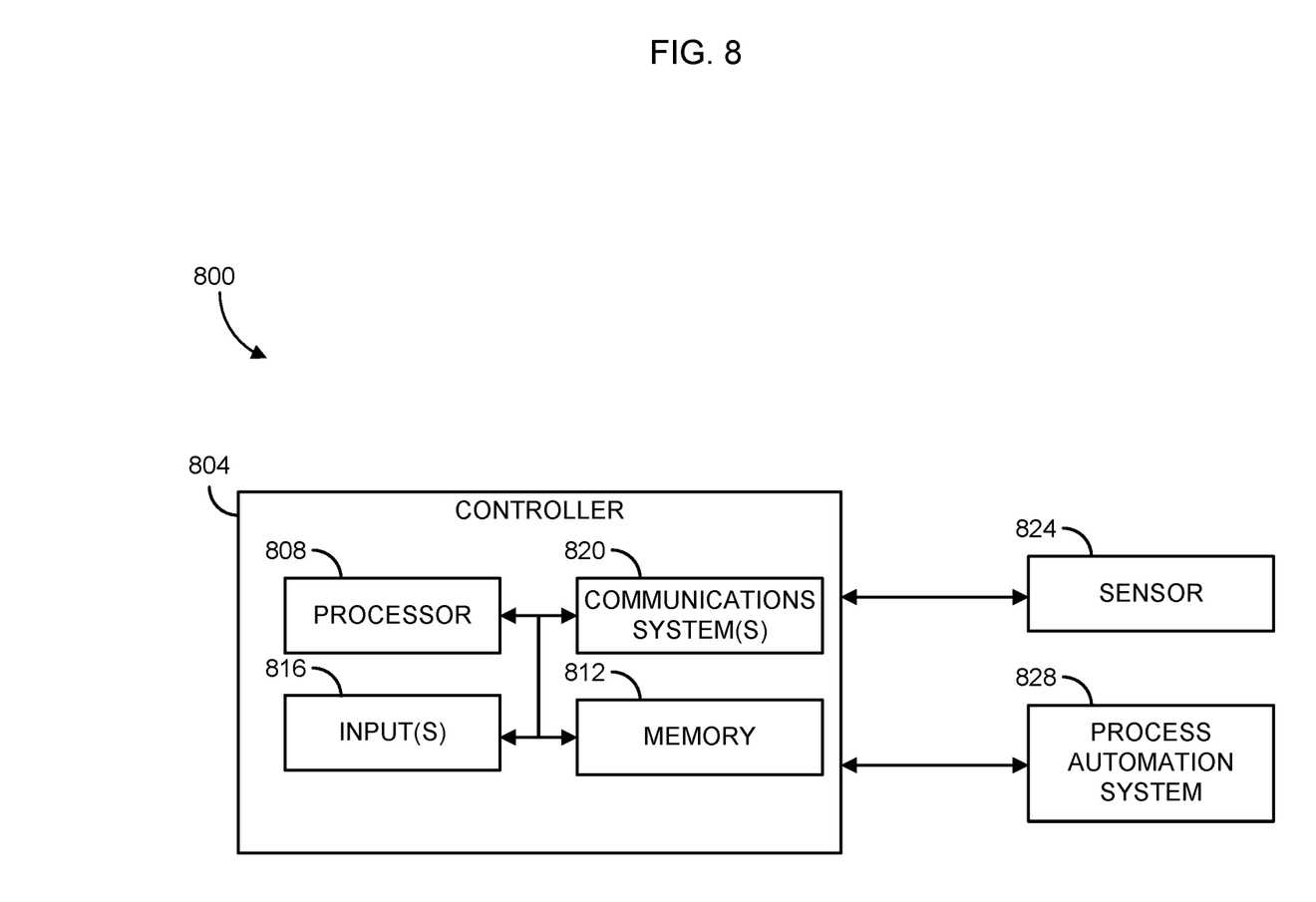
FIG. 8 shows a schematic view of a monitoring system according to some embodiments of the invention.

FIG. 8 illustrates a monitoring system 800 according to some embodiments. The monitoring system 800 can be used to monitor one or more areas for presence of organic liquids. In some embodiments, the monitoring system 800 can include a controller 804, a sensor 824, and a process automation system 828. In some embodiments, the controller 804 can include a processor 808, a memory 812, one or more inputs 816, and one or more communication systems 820.

In some embodiments, the controller 804 can be coupled to the sensor 824 to provide power to the sensor and/or receive a signal from the sensor 824. In some embodiments, the sensor 824 can be the sensor 100 in FIG. 1 and/or the sensor 600 in FIG. 6. In some embodiments, the controller 804 can be coupled to the process automation system 828 to provide the signal from the sensor 824 (e.g., the raw signal or a formatted version of the signal) to the process automation system 828, which may provide remote monitoring of the sensor 824. For example, in some embodiments, the sensor 824 can communicate raw signals, processed resistance measurements, signals indicative of presence/absence of substances (e.g., high/low signals based on a comparison of sensed resistance measurements to threshold resistance values), or other signals to the controller 804. Furthermore, in some embodiments, the controller 804 can be coupled to multiple sensors 824.

In some embodiments, the processor 808 can be any suitable hardware processor or combination of processors, such as a central processing unit (CPU), a graphics processing unit (GPU), a microcontroller (MCU), an application specific integrated circuit (ASIC), a field programmable gate array (FPGA), etc. In some embodiments, inputs 816 can include any suitable input devices and/or sensors that can be used to receive the signal from the sensor 824. In some embodiments, the memory 812 can include any suitable storage device or devices that can be used to store instructions, values (such as threshold resistance values), etc., that can be used, for example, by the processor 808 to communicate with the process automation system 828 via the communications system(s) 820, etc. The memory 812 can include any suitable volatile memory, non-volatile memory, storage, or any suitable combination thereof. For example, the memory 812 can include RAM, ROM, EEPROM, one or more flash drives, one or more hard disks, one or more solid state drives, one or more optical drives, etc. In some embodiments, the memory 812 can have encoded thereon a computer program for controlling operation of the controller 804.

In some embodiments, the communications systems 820 can include one or more transceivers, one or more communication chips, and/or chip sets, etc. In a more particular example, the communications systems 820 can include hardware, firmware, and/or software that can be used to establish a Wi-Fi connection, a Bluetooth connection, a cellular connection, an Ethernet connection, etc.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. An organic liquid sensor configured to output a signal corresponding to the presence of one or more organic liquids and comprising:
    a circuit board;
    an electronic monitoring circuit mounted on a first end of the circuit board, wherein the circuit board comprises a nonconductive surface that extends from the electronic monitoring circuit to a second, opposite end of the circuit board; and
    a sensor film deposited on the nonconductive surface of the circuit board, the sensor film comprising a first length on a first side of the circuit board, a second length on the first side of the circuit board, and a bridge portion on the first side of the circuit board, the first length and the second length being electrically and physically separated by a gap extending through an entire thickness of the circuit board and the bridge portion being electrically coupled to the first length and the second length, wherein the first length, the second length, and the bridge portion comprise the same material and are deposited on the nonconductive surface,
    wherein at least a portion of the nonconductive surface of the circuit board is etched to improve adhesion of the sensor film onto the circuit board,
    wherein the electronic monitoring circuit is configured to detect a resistance of the sensor film.

2. The organic liquid sensor of claim 1, wherein the bridge portion is directly coupled to the first length and the second length.

3. The organic liquid sensor of claim 1, wherein the circuit board comprises a flat surface, and wherein the first length, the second length, and the bridge portion are arranged on the flat surface.

4. The organic liquid sensor of claim 1, wherein the electronic monitoring circuit comprises a first terminal and a second terminal, the first terminal electrically coupled to the first length, and the second terminal electrically coupled to the second length.

5. The organic liquid sensor of claim 4, wherein the first terminal, the first length, the bridge portion, the second length, and the second terminal are electrically coupled in series without any conductive metals exposed to an outside environment.

6. The organic liquid sensor of claim 1, wherein the one or more organic liquids comprises at least one of diesel fuel, gasoline, or jet fuel.

7. The organic liquid sensor of claim 1, wherein the electronic monitoring circuit is coupled to the sensor film and configured to determine the resistance of the sensor film and output the signal corresponding to the presence of the one or more organic liquids based on the resistance of the sensor film.

8. The organic liquid sensor of claim 7, wherein the resistance of the sensor film increases in the presence of the one or more organic liquids.

9. The organic liquid sensor of claim 1, wherein the sensor film is deposited on the first side of the circuit board in a U-shape pattern.

10. The organic liquid sensor of claim 1, further comprising a primer layer deposited on the nonconductive surface, wherein the sensor film is deposited on the primer layer.

11. The organic liquid sensor of claim 1, wherein the sensor film comprises an elastomer filled with conductive particles.

12. The organic liquid sensor of claim 1, wherein the organic liquid sensor is configured to couple to a controller and output the signal to the controller.

13. An organic liquid monitoring system comprising:
    a controller comprising a memory and a processor; and
    an organic liquid sensor configured to output a signal corresponding to the presence of one or more organic liquids, the organic liquid sensor comprising:
        a circuit board,
        an electronic monitoring circuit mounted on a first end of the circuit board, wherein the circuit board comprises a nonconductive surface that extends from the electronic monitoring circuit to a second, opposite end of the circuit board, and
        a sensor film deposited on the nonconductive surface of the circuit board, the sensor film comprising a first length on a first side of the circuit board, a second length on the first side of the circuit board, and a bridge portion on the first side of the circuit board, the first length and the second length being electrically and physically separated by a gap extending through an entire thickness of the circuit board and the bridge portion being electrically coupled to the first length and the second length, wherein the first length, the second length, and the bridge portion comprise the same material and are deposited on the nonconductive surface,
        wherein at least a portion of the nonconductive surface of the circuit board is etched to improve adhesion of the sensor film onto the circuit board,
        wherein the electronic monitoring circuit is configured to detect a resistance of the sensor film,
        wherein the controller is coupled to the organic liquid sensor and configured to receive the signal corresponding to the presence of the one or more organic liquids.

14. The system of claim 13, wherein the circuit board comprises a flat surface, and wherein the first length, the second length, and the bridge portion are arranged on the flat surface.

15. The system of claim 13, wherein the electronic monitoring circuit comprises a first terminal and a second terminal, the first terminal electrically coupled to the first length, and the second terminal electrically coupled to the second length, wherein the first terminal, the first length, the bridge portion, the second length, and the second terminal are electrically coupled in series without any exposed conductive metals.

16. An organic liquid sensor configured to output a signal corresponding to the presence of one or more organic liquids and comprising:
  a circuit board;
  an electronic monitoring circuit mounted on the circuit board; and
  a U-shaped sensor film deposited on a surface of the circuit board, the U-shaped sensor film comprising a first length, a second length, and a bridge portion between the first length and the second length, the first length and the second length being electrically separated by a gap extending through an entire thickness of the circuit board and the bridge portion being electrically coupled to the first length and the second length, wherein the first length, the second length, and the bridge portion comprise the same material,
  wherein the electronic monitoring circuit is located on the surface of circuit board adjacent a first end of the circuit board and the bridge portion is located on a nonconductive portion of the surface of the circuit board adjacent an opposite second end of the circuit board,
  wherein the electronic monitoring circuit is configured to detect a resistance of the sensor film.

* * * * *

UNITED STATES PATENT AND TRADEMARK OFFICE
CERTIFICATE OF CORRECTION

| | | |
|---|---|---|
| PATENT NO. | : 12,422,391 B2 | |
| APPLICATION NO. | : 17/005094 | |
| DATED | : September 23, 2025 | |
| INVENTOR(S) | : Wesley Dong et al. | |

It is certified that error appears in the above-identified patent and that said Letters Patent is hereby corrected as shown below:

In the Specification

Column 9, Table Heading, "Dry Type" should be --Type--.

Column 9, Table Heading, "Day Resistance (KΩ)" should be --Dry Resistance (KΩ)--.

Signed and Sealed this
Ninth Day of December, 2025

John A. Squires
*Director of the United States Patent and Trademark Office*